(12) United States Patent
Boege

(10) Patent No.: US 7,221,449 B2
(45) Date of Patent: May 22, 2007

(54) APPARATUS FOR ASSAYING FLUOROPHORES IN A BIOLOGICAL SAMPLE

(75) Inventor: Steven J. Boege, San Mateo, CA (US)

(73) Assignee: Applera Corporation, Foster City, CA (US)

( * ) Notice: Subject to any disclaimer, the term of this patent is extended or adjusted under 35 U.S.C. 154(b) by 318 days.

(21) Appl. No.: 10/879,374

(22) Filed: Jun. 28, 2004

(65) Prior Publication Data

US 2005/0286047 A1 Dec. 29, 2005

(51) Int. Cl.
*G01J 3/30* (2006.01)

(52) U.S. Cl. ...................................... 356/317

(58) Field of Classification Search ......... 356/300–334
See application file for complete search history.

(56) References Cited

U.S. PATENT DOCUMENTS

| | | | |
|---|---|---|---|
| 4,968,117 A | 11/1990 | Chern et al. | |
| 5,141,312 A | 8/1992 | Thompson et al. | |
| 5,428,438 A | 6/1995 | Komine | |
| 5,452,125 A | 9/1995 | White et al. | |
| 5,561,554 A | 10/1996 | White et al. | |
| 6,100,974 A | 8/2000 | Reininger | |
| 6,522,717 B1* | 2/2003 | Murakami et al. | 378/43 |
| 6,545,758 B1 | 4/2003 | Sandstrom | |
| 6,567,163 B1 | 5/2003 | Sandstrom | |
| 6,667,830 B1 | 12/2003 | Iketaki et al. | |
| 2002/0101587 A1* | 8/2002 | Wilson et al. | 356/328 |
| 2003/0174324 A1 | 9/2003 | Sandstrom | |

FOREIGN PATENT DOCUMENTS

| | | |
|---|---|---|
| EP | 1 221 598 A1 | 7/2002 |
| WO | WO 02/059584 | 8/2002 |
| WO | WO 03/064699 | 8/2003 |

OTHER PUBLICATIONS

Partial International Search Report, PCT/US2005/022947, Mailed Dec. 14, 2005.

* cited by examiner

Primary Examiner—Gregory J. Toatley, Jr.
Assistant Examiner—Isiaka O. Akanbi

(57) ABSTRACT

An optical device adapted to detect fluorescence from a biological sample. The optical device includes an optical relay to collect fluorescence emitted by the fluorophores and to direct the collected fluorescence towards a detector.

39 Claims, 9 Drawing Sheets

APPARATUS FOR ASSAYING FLUOROPHORES IN A BIOLOGICAL SAMPLE

DESCRIPTION OF THE INVENTION

1. Field

The present teaching relates to methods and systems for fluorescent detection in biological samples.

2. Introduction

Capillary electrophoresis allows high-throughput assaying of fluorophores. This technique can employ one or multiple capillaries, as well as multiple types of dyes. Because optical systems with multiple lenses and refractive elements can introduce aberration, the location of the detector can be moved depending on the type of dye to minimize the distortion. It is desirable to detect the multiple types of dyes for each spectral range of detection without introducing aberration or changing the location of the detector.

SUMMARY

In various embodiments, the present teachings can provide an optical device for fluorescence detection from biological samples including a detector, a first optical relay including a convex reflector, a first concave reflector, and a second concave reflector, wherein the second concave reflector includes a first filter that reflects fluorescence emitted by fluorophores and that transmits an excitation light, and an excitation light source disposed such that the excitation light couples through the second concave reflector.

In various embodiments, the present teachings can provide an optical device for fluorescence detection from biological samples including a excitation light source, a detector, and a first optical relay including a concave reflector, and a convex reflector, wherein the convex reflector includes a diffraction grating.

In various embodiments, the present teachings can provide an optical device for fluorescence detection from biological samples including an excitation light source, a detector, a first optical relay including a convex reflector, a first concave reflector, and a second concave reflector, and a lens disposed to vary a collection angle of the optical device.

In various embodiments, the present teachings can provide an optical device for fluorescence detection from biological samples including an excitation light source disposed to excite fluorophores to emit fluorescence, a detector, a first Schwarzschild telescope disposed to collect fluorescence emitted by fluorophores, a wavelength separation system disposed to reject the excitation light and transmit fluorescence collected by the first Schwarzschild telescope, and a focusing system disposed to focus fluorescence transmitted by the wavelength separation system onto the detector.

It is to be understood that both the foregoing general description and the following detailed description are exemplary and explanatory only and are not restrictive of the invention as claimed.

The accompanying drawings, which are incorporated in and constitute a part of this specification, illustrate some embodiments of the invention, and together with the description serve to explain the principles of the invention.

DESCRIPTION OF VARIOUS EMBODIMENTS

Figure 1:
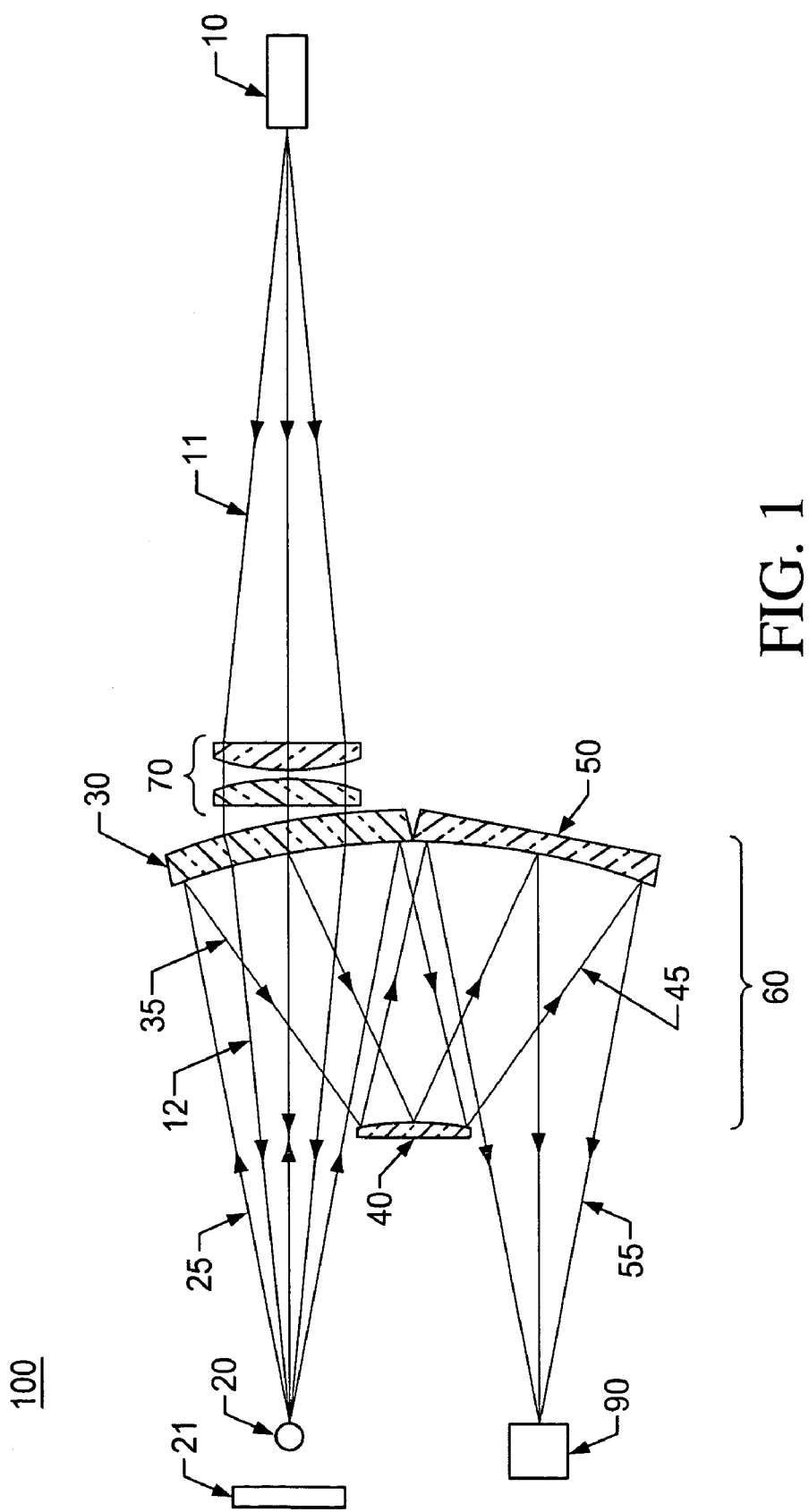
FIG. 1 illustrates a representative optical system according to various embodiments of the present teachings.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Wherever possible, the same reference numbers will be used throughout the drawings to refer to the same or like parts.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose. In the event that one or more of the incorporated literature and similar materials differs from or contradicts this application, including but not limited to defined terms, term usage, described techniques, or the like, this application controls.

The term "light source" and "excitation light source" as used herein refers to a source of irradiance that can provide excitation that results in fluorescent emission. Light sources can include, but are not limited to, white light, halogen lamp, lasers, solid state laser, laser diode, micro-wire laser, diode-pumped solid state lasers (DSSL), vertical-cavity surface-emitting lasers (VCSEL), LEDs, phosphor coated LEDs, organic LEDs (OLED), thin-film electroluminescent devices (TFELD), phosphorescent OLEDs (PHOLED), inorganic-organic LEDs, LEDs using quantum dot technology, LED arrays, an ensemble of LEDs, a floodlight system using LEDs, and/or white LEDs, filament lamps, arc lamps, gas lamps, and fluorescent tubes. Light sources can have high irradiance, such as lasers, or low irradiance, such as LEDs. The different types of LEDs mentioned above can have a medium to high irradiance.

The term "detector" as used herein refers to any component, portion thereof, or system of components that can detect light including a charged coupled device (CCD), back-side thinned, cooled CCD, front-side illuminated CCD, a CCD array, a photodiode, a photodiode array, a photomultiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, using for example, a computer, or other signal processing system.

The term "fluorophore" as used herein refers to fluorescent dyes that respond to an excitation source by emitting a fluorescent light. The fluorophores can be attached to particular molecules so as to act as labels during sample interrogation.

The term "sample" as used herein refers to any biological or chemical substance in solution with fluorophores that can be excited by excitation light to emit fluorescent light. The term "capillary" refers to a transparent structure that provides containment to the sample. In embodiments, a sample can be contained in one or more capillaries. Although samples are depicted in the accompanying figures as contained in one or multiple capillaries, the figures are exemplary and not intended to limit the number of capillaries that can contain the sample.

In various embodiments, as illustrated in FIG. 1, an optical device 100 can include a light source 10, a sample 20, an optical relay 60, and a detector 90. In various embodiments, optical relay 60 can be an Offner relay. Optical reply 60 can include a convex reflector 40, a first concave reflector 50, and a second concave reflector 30. Second concave reflector 30 can include a filter, such as, for example, a short pass coating that reflects fluorescence emitted by sample 20 and that transmits an excitation light provided by light source 10. Examples of the general arrangement and operation of these components will now be described.

Light source 10 can be disposed such that an excitation light 11 emitted by light source 10 couples through second concave reflector 30 to irradiate sample 20. In various embodiments, light source 10 can further include a light pipe (not shown) to reformat the excitation light to increase irradiance to a desired region of sample 20. In various embodiments, light source 10 can also include a mixing rod (not shown) to achieve uniform light from a non-uniform light source.

Second concave reflector 30 directs an excitation 12 towards sample 20. Excitation light 12 causes one or more dyes in sample 20 to emit light in the form of, for example, fluorescence. Second concave reflector 30 is disposed to collect a fluorescence 25, emitted by sample 20, and reflect the collected fluorescence towards convex reflector 40. Convex reflector 40 collects a fluorescence 35, reflected from second concave reflector 30, and reflects the collected fluorescence towards first concave reflector 50. First concave reflector 50 collects a fluorescence 45, reflected from convex reflector 40, and reflects the collected fluorescence towards detector 90. Detector 90 receives a fluorescence 55 reflected from concave reflector 50.

In various embodiments, optical system 100 can further include a first optical element 70 to increase convergence of excitation light 11 onto second concave reflector 30. First optical element 70 can include, for example, condenser optics, Fresnel elements, an excitation filter, and other optical elements know to one of skill in the art. Although depicted in FIG. 1 as including two components, first optical element 70 can include one or more components.

Optical system 100 can further include a second optical element 21 disposed to reflect excitation light 11 and reflect fluorescence emitted by sample 20. Optical element 21 thereby reflects the excitation light onto sample 20 and reflects fluorescence emitted by sample towards optical relay 60.

Figure 2:
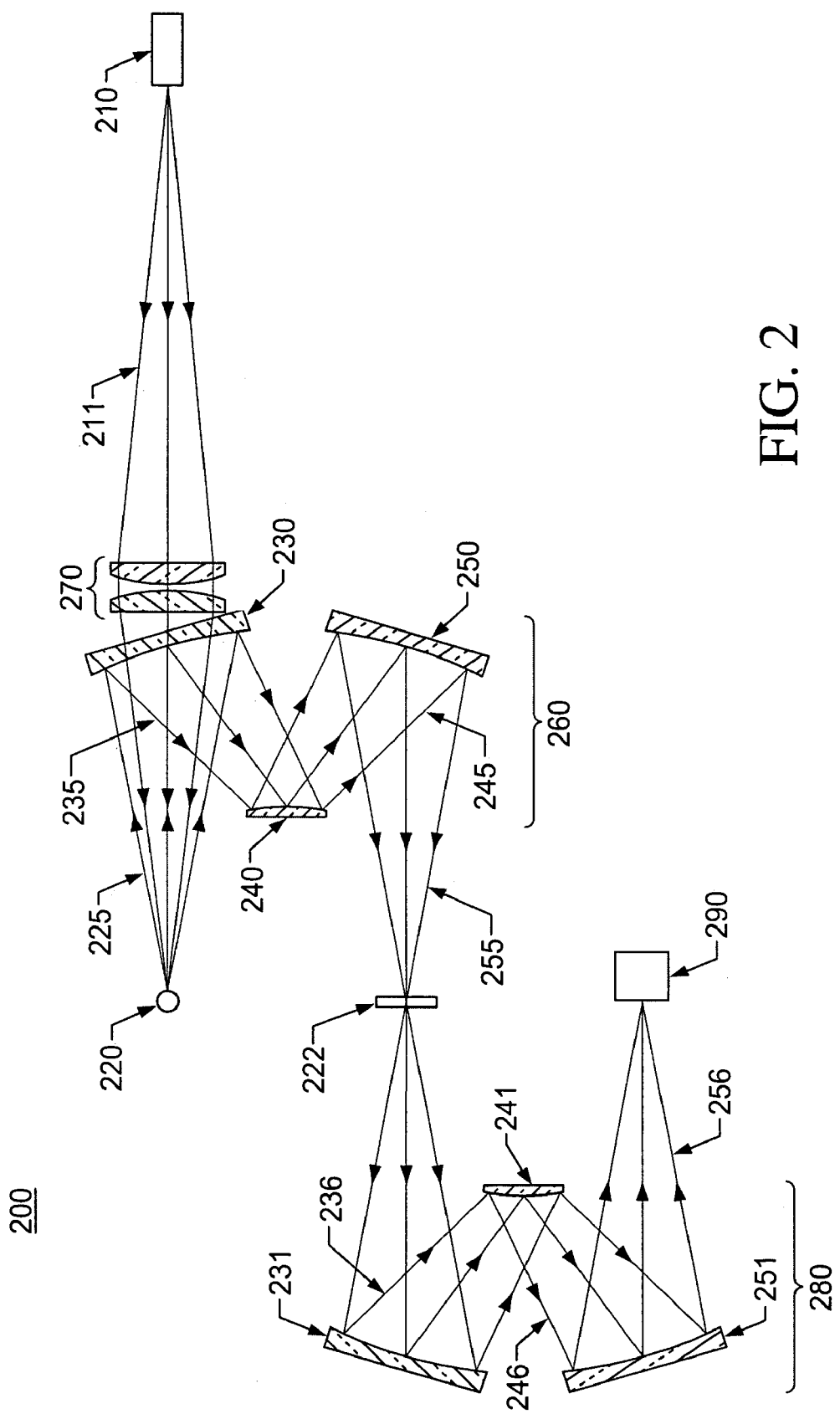
FIG. 2 illustrates a representative optical system including two optical relays according to various embodiments of the present teachings.

In various embodiments, optical device 100 can include a second optical relay. As illustrated in FIG. 2, an optical device 200 can include a first optical relay 260, a second optical relay 280, and a filter 222. First optical relay 260 can include a convex reflector 240, a first concave reflector 250, and a second concave reflector 230. Second concave reflector 230 can include a filter, such as, for example, a short pass coating that reflects fluorescence emitted by a sample 220 and that transmits an excitation light provided by a light source 210. Second optical relay 280 can include a third concave reflector 231, a fourth concave reflector 251, and a further convex reflector 241. In various embodiments, a single concave reflector can be used in place of third concave reflector 231 and fourth concave reflector 251.

Light source 210 can be disposed such that an excitation light 211 emitted by light source 210 couples through second concave reflector 230 to cause one or more dyes in sample 220 to emit light in the form of, for example, fluorescence. Second concave reflector 230 collects a portion of a fluorescence 225, emitted by sample 220, and reflects the collected fluorescence towards convex reflector 240. Convex reflector 240 collects a fluorescence 235, reflected by second concave reflector 230, and reflects the collected fluorescence towards first concave reflector 250. Concave reflector 250 collects a fluorescence 245, reflected from concave reflector 240, and reflects the collected fluorescence towards filter 222. A fluorescence 255, reflected by concave reflector 250, couples through filter 222 towards second optical relay 280. Filter 222 and the coating on reflector 230 act in concert to help prevent the rejection light from entering the second relay. High levels of rejection can be desirable. By dividing the total rejection between two optics, each one can have a lower individual blocking level, resulting in higher manufacturing yield and lower manufacturing cost.

Third concave reflector 231 collects fluorescence 255 and reflects the collected fluorescence towards further concave reflector 241. Further convex reflector 241 collects a fluorescence 236, reflected from third concave reflector 231, and reflects the collected fluorescence towards fourth concave reflector 251. Fourth concave reflector 251 collects a fluorescence 246, reflected from the further convex reflector 241, and reflects the collected fluorescence towards detector 290. Detector 290 receives a fluorescence 256 reflected from fourth concave reflector 251.

In various embodiments, further convex reflector 241 can include a diffraction grating to cause diffractive and interference effects to concentrate fluorescence 236 into discrete spectral orders. Optical system 200 can be used as a spectrograph to measure the spectra of fluorescence emitted by sample 220 and/or used to image sample 220. Moreover, in various embodiments, light source 210 can be, for example, a slit that can be backlit by a lamp. Additionally, in various embodiments, one or both of first optical relay 260 and second optical relay 280 can be an Offner relay.

Figure 3:
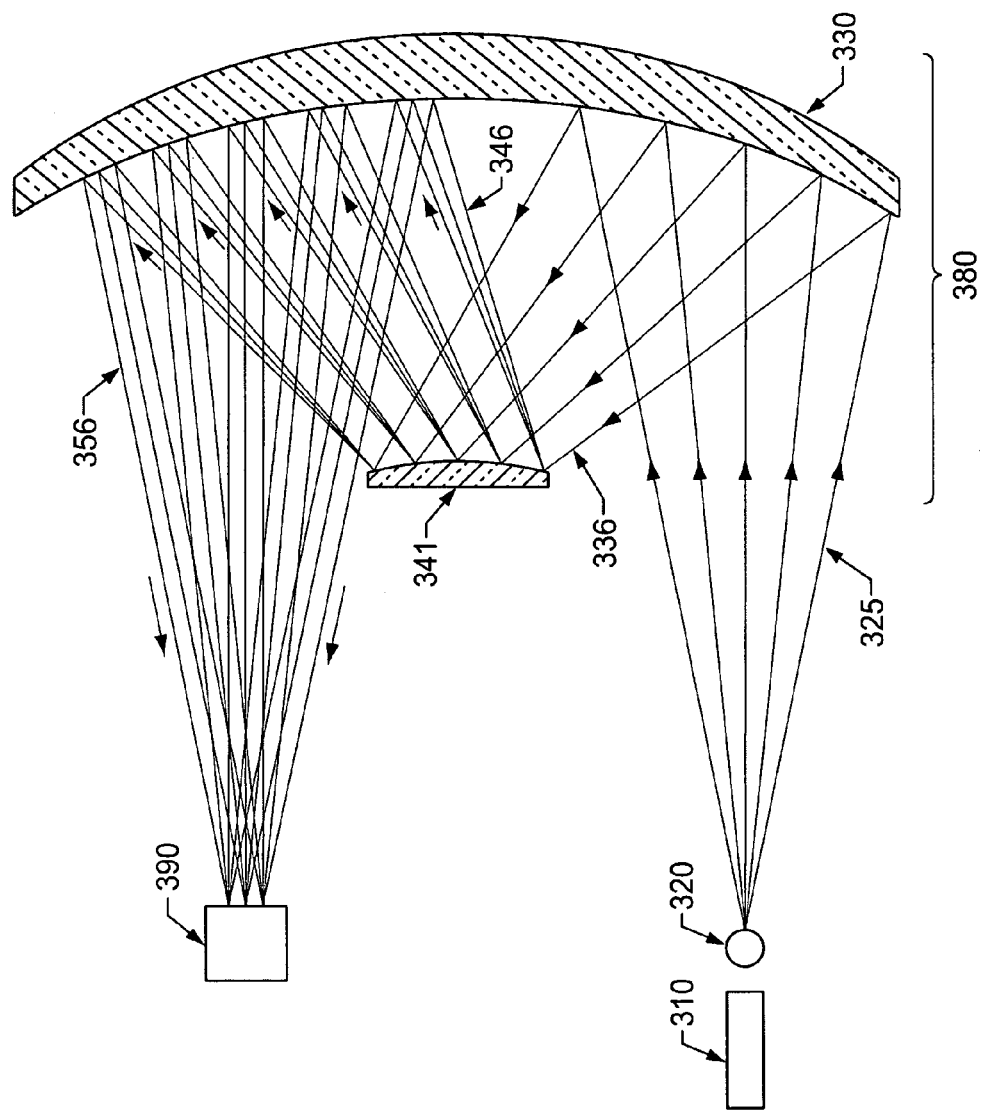
FIG. 3 illustrates a representative optical system that provides spectrographic information according to various embodiments of the present teachings.

In various embodiments, as illustrated in FIG. 3, an optical device 300 can include a light source 310, a detector 390, and a first optical relay 380. First optical relay 380 can include a concave reflector 330 and a convex reflector 341. Convex reflector 341 can include a diffraction grating so that spectrographic information can be gathered. Examples of the general arrangement and operation of these components will now be described.

Light source 310 provides an excitation light to cause a sample 320 to emit a fluorescence 325. Concave reflector 330 collects a portion of fluorescence 325 and reflects the collected portion of fluorescence towards convex reflector 341. Convex reflector 341 can include a diffraction grating that can collect a fluorescence 336 reflected from concave reflector 330. Convex reflector 341 including a diffraction grating causes diffractive and interference effects to concentrate fluorescence 336 into discrete spectral orders. Lines 346 in FIG. 3 represent these discrete spectral orders. Concave reflector 330 collects a fluorescence 346 including spectral information and reflects the collected fluorescence including spectral information towards detector 390. Detector 390 receives fluorescence 356 including spectral information reflected from convex reflector 330. In various embodiments, optical relay 380 can be an Offner relay.

Figure 4:
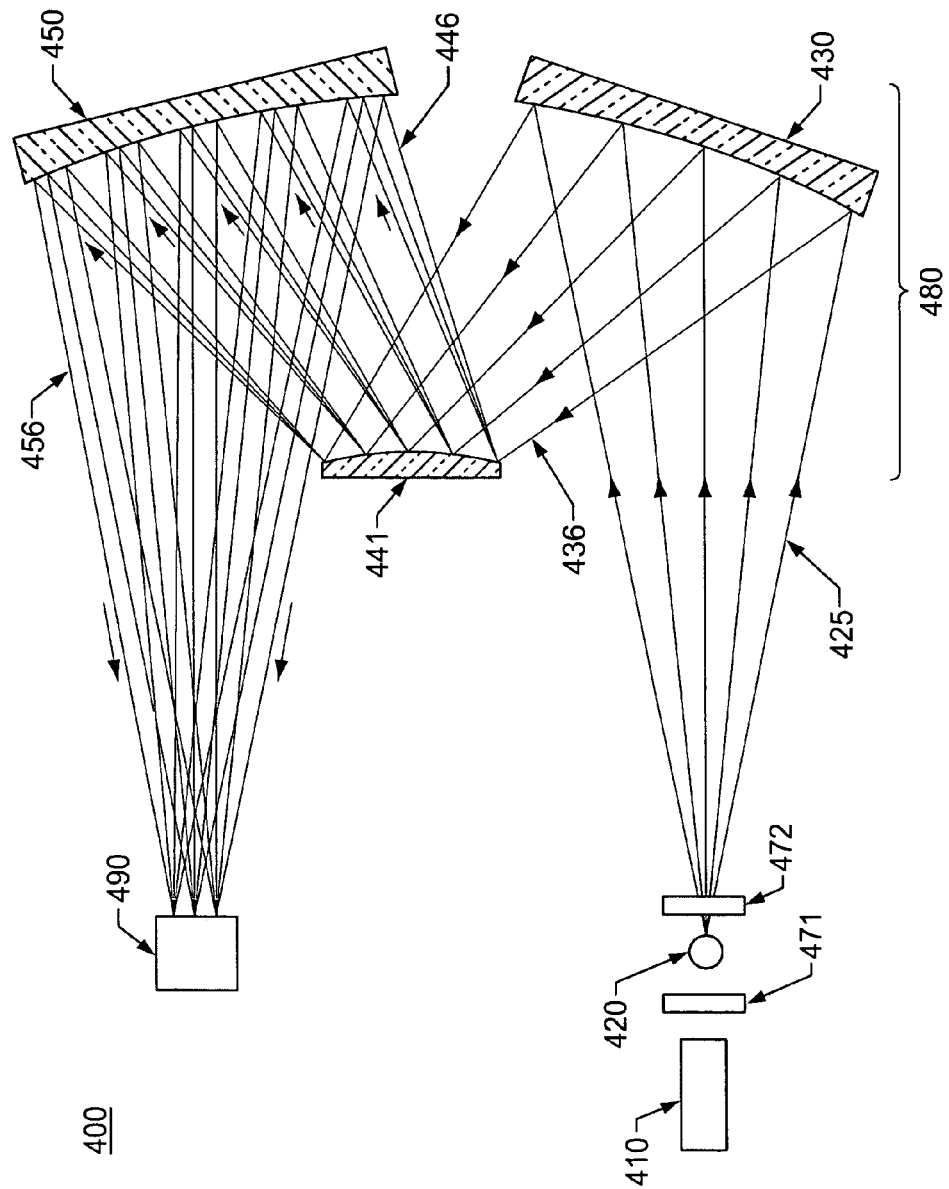
FIG. 4 illustrates another representative optical system that provides spectrographic information according to various embodiments of the present teachings.

In various embodiments, two concave reflectors can be used in place of concave reflector 330. As depicted in FIG. 4, optical system 400 can include an optical relay 480. Optical relay 480 can include a first concave reflector 430 and a second concave reflector 450. In operation, light source 410 provides an excitation light to cause a sample 420 to emit a fluorescence 425. First concave reflector 430 collects a portion of fluorescence 425 and reflects the collected portion of fluorescence towards convex reflector 441. Convex reflector 441 can include a diffraction grating that can collect a fluorescence 436 reflected from first concave reflector 430. Convex reflector 441 causes diffractive and interference effects to concentrate collected portion of fluorescence 436 into discrete spectral orders. Second concave reflector 450 collects a fluorescence 446, reflected from convex reflector 441, and reflects the collected portion of fluorescence towards detector 490. Detector 490 receives a fluorescence 456 reflected by second concave reflector 450. In various embodiments, optical relay 480 can be an Offner relay.

In various embodiments, optical system 400 can include a first filter 471 disposed to transmit the excitation light and reflect fluorescence emitted by sample 420. By reflecting fluorescence emitted by sample 420, first filter 471 can allow fluorescence that might otherwise go uncollected to be collected by first concave reflector 430.

Optical system 400 can further include a second filter 472 disposed to reflect the excitation light and transmit fluorescence emitted by sample 420. Second filter 471 transmits fluorescence emitted by sample 420 and reflected by first filter 471. By reflecting excitation light back towards sample 420, second filter 472 can increase the excitation light that falls on sample 420.

Figure 5:
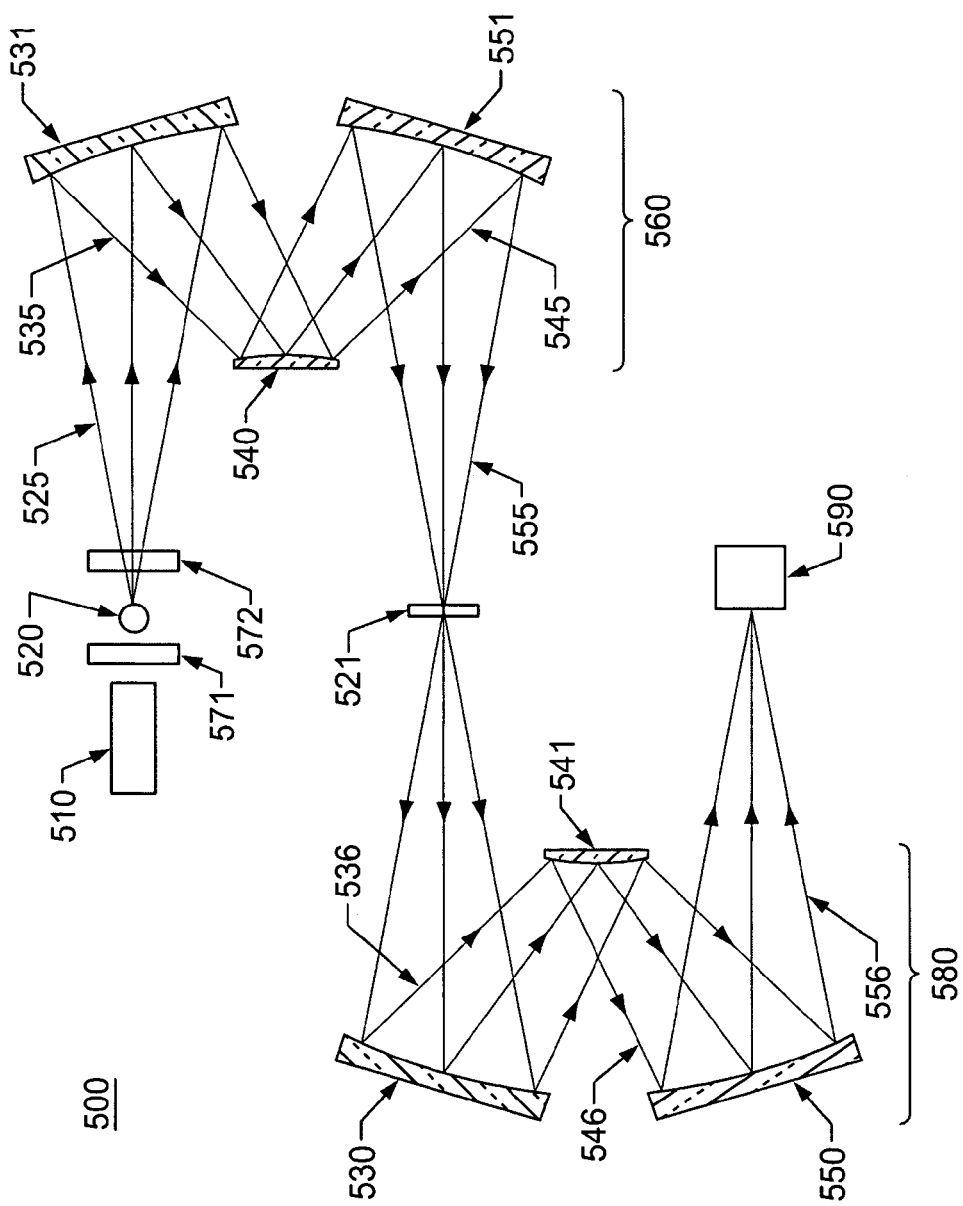
FIG. 5 illustrates another representative optical system including two optical relays according to various embodiments of the present teachings.

In various embodiments, as shown in FIG. 5, optical system 500 can include a first optical relay 560, a second optical relay 580, and a third filter 521. First optical rely 560 can include a first concave reflector 531, a second concave reflector 551, and a convex reflector 540. Second optical relay 560 can include a third concave reflector 530, a fourth concave reflector 550, and a further convex reflector 541. Although depicted in FIG. 5 as disposed before second optical relay 580, in various embodiments, first optical relay 560 can be disposed after second optical relay 580 with respect to the optical path from a sample 520 to a detector 590. In various embodiments, a single reflector, such as reflector 330 depicted in FIG. 3, can be used instead of concave reflectors 531 and 551. In various embodiments, a single concave reflector can also be used instead of concave reflectors 530 and 440. Third filter 521 can be disposed between first optical relay 560 and second optical relay 580. Examples of the general arrangement and operation of these components will now be described.

In various embodiments, light source 510 provides an excitation light to cause sample 520 to emit a fluorescence 525. A first filter 571 can be disposed between light source 510 and sample 520 to transmit the excitation light and reflect fluorescence 525 emitted by sample 520. This arrangement can allow first filter 571 to reflect fluorescence, some of which would otherwise not have been collected, towards first optical relay 560. A second filter 572 can be disposed between sample 520 and first optical relay 560. Second filter 572 can transmit fluorescence 525 emitted by sample 520 and reflect the excitation light. This can increase the excitation light that falls on sample 520 by reflecting excitation light from second filter 572 onto sample 520.

First concave mirror 531 collects a portion of fluorescence 525 and reflects the collected portion of fluorescence to convex mirror 540. Convex mirror 540 collects a fluorescence 535, reflected by first concave mirror 531, and reflects the collected fluorescence towards second concave mirror 551. Second concave mirror 551 collects a fluorescence 545, reflected by convex mirror 540, and reflects the collected fluorescence towards third filter 521. Third filter 521 can be disposed to transmit a fluorescence 555, reflected by second concave mirror 551, and to reflect excitation light that was previously not reflected by second filter 571.

Fluorescence 555 transmitted by third filter 521 is collected by third concave reflector 530 and reflected towards further convex reflector 541. Further convex reflector 541 collects a fluorescence 536, reflected by third concave reflector 530, and reflects the collected fluorescence towards fourth concave reflector 550. In various embodiments, further convex reflector 541 can include a diffraction grating to cause diffractive and interference effects to concentrate fluorescence 536 into discrete spectral orders. Fourth concave reflector 550 collects a fluorescence 546, reflected from convex reflector 541, and reflects the collected fluorescence towards detector 590. Detector 590 receives a fluorescence 556 reflected by fourth concave reflector 550.

Figure 6:
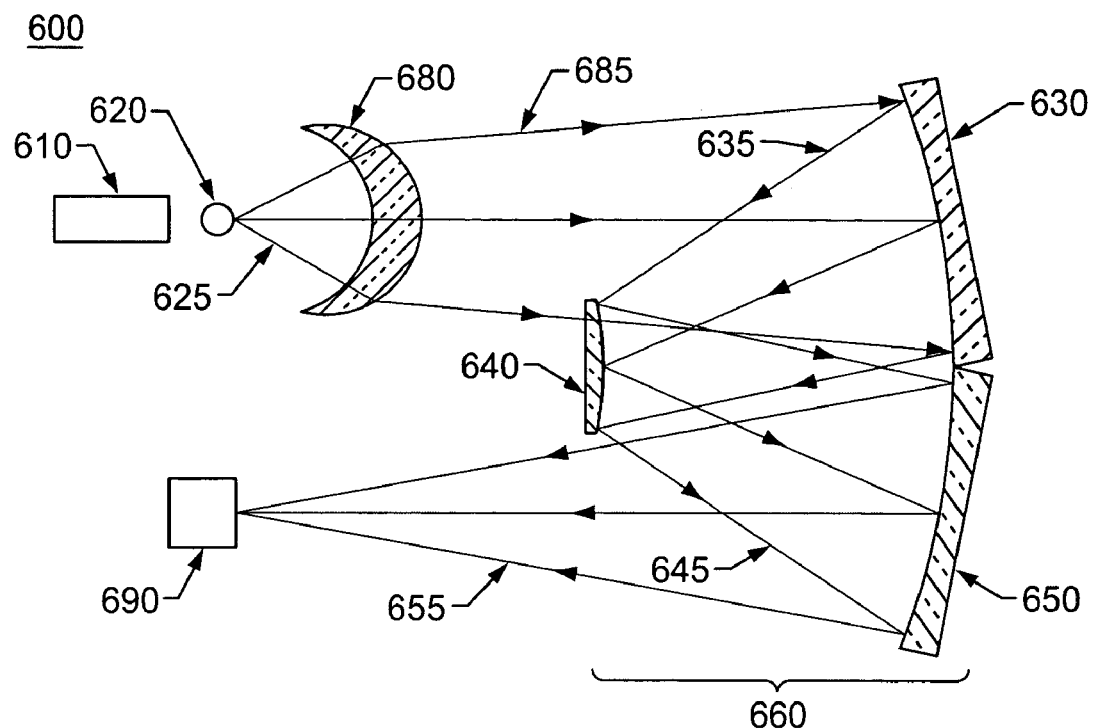
FIG. 6 illustrates another representative optical system according to various embodiments of the present teachings.

In various embodiments, the optical systems described herein can include optical elements, for example, that increase the collection angle of fluorescence emitted by a sample. As shown in FIG. 6, optical system 600 can include a light source 610, a detector 690, an optical relay 660, and an optical element 680. For illustrative purposes, optical relay 660 is depicted in FIG. 6 as including a first concave reflector 630, a second concave reflector 650, and a convex reflector 640. Optical relay 660, however, can include other optical relay configuration, such as, for example, those described herein. Optical element 680 can increase the convergence of fluorescence 625, thereby increasing the collection of fluorescence by first concave reflector 630. Optical element 680 can be, for example, an aplanat. As used herein, the term "aplanat" refers to an aplanatic lens that introduces substantially no additional spherical aberration or coma. Due to its shape, aplanat 680 increases the collection angle of fluorescence and increases the amount of fluorescence 625 directed towards first convex reflector 630. In various embodiments, a single concave reflector can be used instead of concave reflectors 630 and 650 as described herein.

Figure 7:
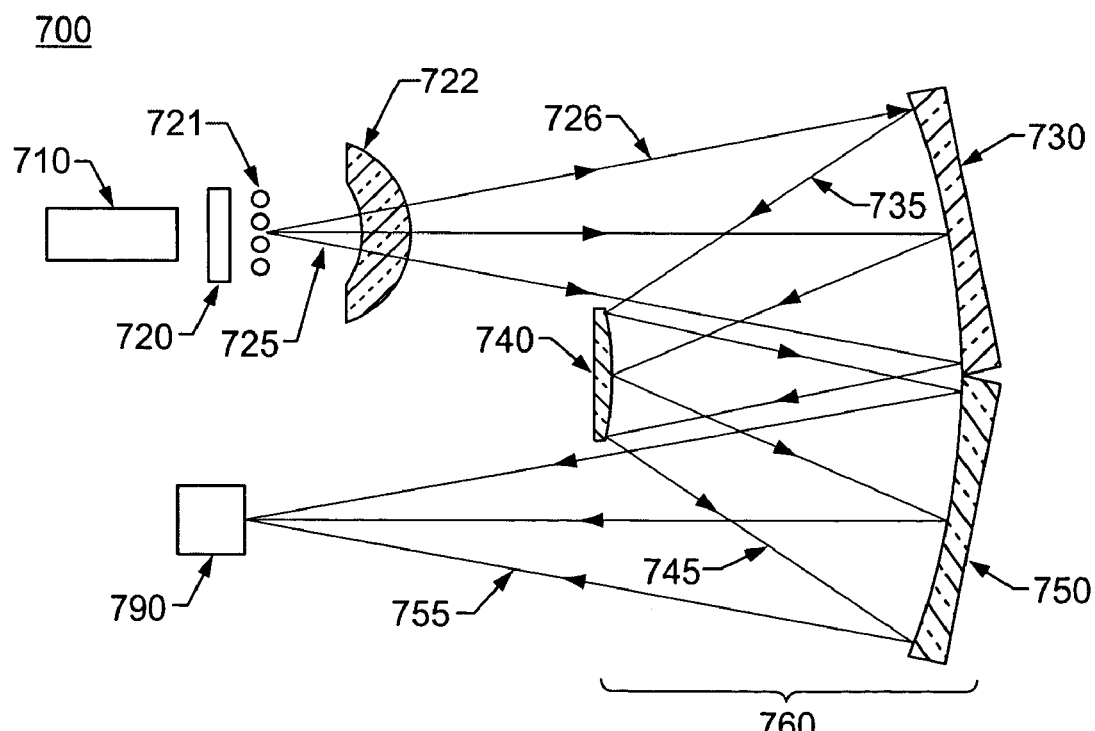
FIG. 7 illustrates another representative optical system according to various embodiments of the present teachings.

In various embodiments, the optical systems described herein can include optical elements, for example, that serve as an excitation filter and as an emission filter. As shown in FIG. 7, optical system 700 can include a light source 710, a detector 790, an optical relay 760, and an optical element 722. For illustrative purposes, optical relay 760 is depicted in FIG. 7 as including a first concave reflector 730, a second concave reflector 750, and a convex reflector 740. Optical relay 760, however, can include other configurations, such as, for example, those described herein. In various embodiments, optical element 721 can include a surface concentric to the plane of sample 720. In various embodiments, optical element 721 can include a long transmit/short reflect coating to transmit fluorescence 725 emitted by sample 720 and to reflect an excitation light from light source 710. This can allow fluorescence emitted by sample 720 to reach detector 790 and excitation light from light source 710 to be imaged back to sample 720.

In various embodiments, optical system 700 can include an excitation filter. As shown in FIG. 7, an excitation filter 720 can be disposed to transmit the excitation light from light source 710 and to reflect the fluorescence emitted by sample 720 back towards optical relay 760. In various embodiments, a single concave reflector can be used instead of concave reflectors 730 and 750 as described herein.

Figure 8:
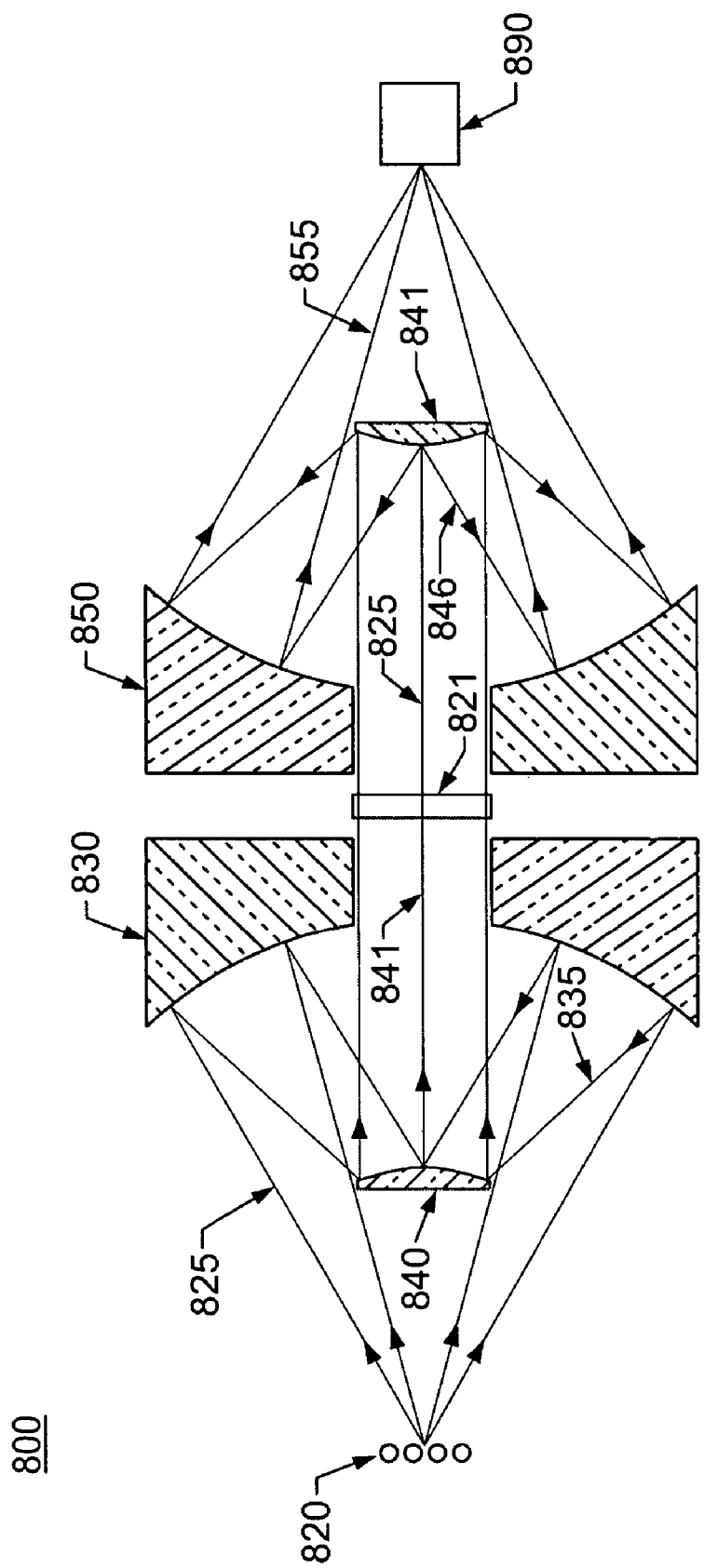
FIG. 8 illustrates a representative optical system including a reflecting telescope according to various embodiments of the present teachings.
Figure 9:
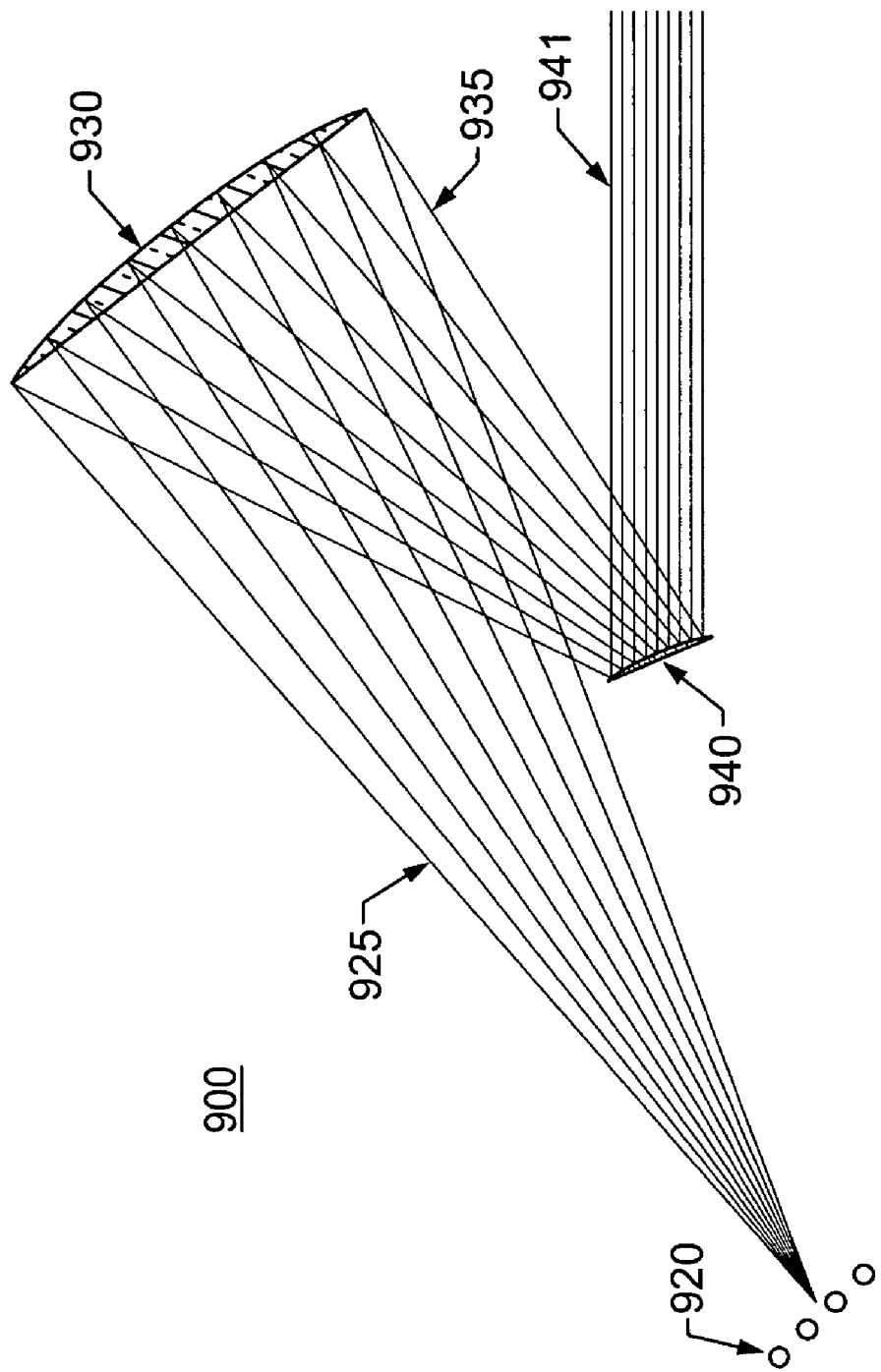
FIG. 9 illustrates a representative optical system including an unobstructed reflecting telescope according to the present teachings.

In various embodiments, as illustrated in FIG. 8, an optical device 800 can include a first reflecting telescope on the left to collect light, a second reflecting telescope on the right to capture the light on a detector, and an optical element 821. First reflecting telescope can include a first concave reflector 830, including an aperture, and a first convex reflector 840. Second reflecting telescope can include a second concave reflector 850, including an aperture, and a second convex reflector 841. In various embodiments, first reflecting telescope and second reflecting telescope can be a Schwarzschild telescope. Examples of the general arrangement and operation of these components will now be described.

In various embodiments, an excitation light causes a sample 820 to emit light, for example in the form of a fluorescence 825. First reflecting telescope can be disposed such that first concave reflector 830 collects a portion of fluorescence 825. First concave reflector 830 reflects the collected portion of fluorescence towards first convex reflector 840. First convex reflector 840 collects a fluorescence 835, reflected by first concave reflector 830, and reflects the collected fluorescence through the first aperture in first concave reflector 830 towards optical element 821.

In various embodiments, optical element 821 can be an emission filter. Emission filter 821 can reflect the excitation light back through the aperture of first concave reflector 830. The excitation light that passes through the first aperture can be reflected by first convex reflector 840 towards first concave reflector 830. First concave reflector 830 can then reflect the excitation light onto sample 820. Excitation filter 821 can couple a fluorescence 841, reflected by first concave reflector 840 through the aperture of the first concave reflector 830, towards second reflecting telescope.

Second reflecting telescope 880 can be disposed such that fluorescence 841, coupled through emission filter 821, passes through the aperture of second concave reflector 850 to reflect from second convex reflector 841. Second concave reflector 850 collects a fluorescence 846 reflected from second convex reflector 841. Second concave reflector 850 reflects the collected fluorescence towards a detector 890. Detector 890 receives a fluorescence 855 reflected by second concave reflector 850.

FIG. 8 represents an obstructed reflecting telescope, as the convex reflector 840 is in the light path. In various embodiments, an unobstructed reflecting telescope 900 can collect light. Excitation light causes a sample 920 to emit light, for example in the form of a fluorescence 925. Unobstructed reflecting telescope 900 can be disposed such that internally concave reflector 930 collects a portion of fluorescence 925. Internally concave reflector 830 reflects the collected portion of fluorescence towards convex reflector 940. Convex reflector 940 collects the fluorescence 935, reflected by internally concave reflector 930. In various embodiments, light can be captured by a detector from internally concave reflector 930 with a reflective telescope similar to that described above.

In various embodiments, a reflecting telescope can be used to collect fluorescence. Its collimated output can be spectrally shaped by filters, gratings, or prisms. The shaped output can be focused by any optical system of positive focal length. FIG. 8 illustrates focusing with a second reflecting telescope. In various embodiments, focusing can be achieved by regular refracting lenses, spherical or aspheric mirrors, or paraboloid mirrors.

Figure 10:
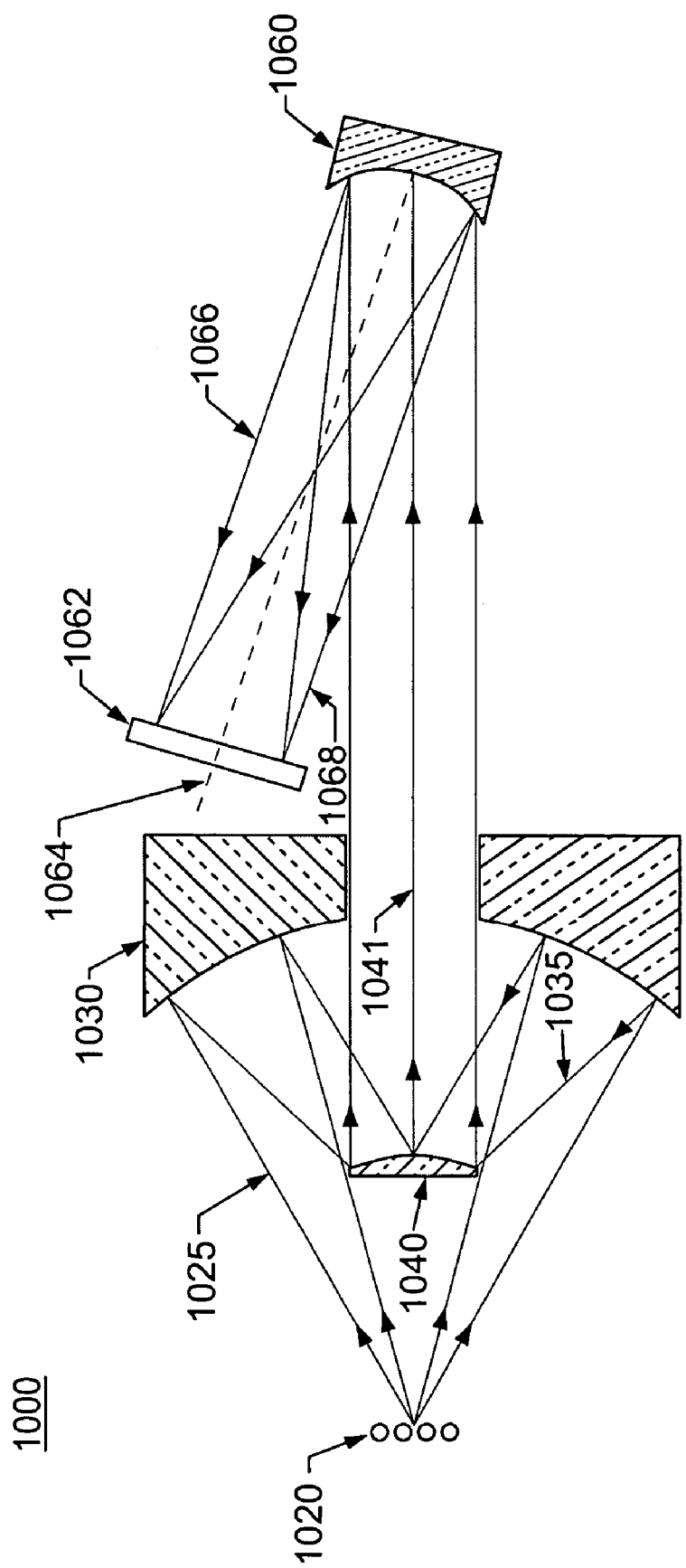
FIG. 10 illustrates a representative optical system including a reflecting telescope and spectrographic grating according to the present teachings.

In various embodiments, the output of a reflecting telescope can be fed into a spectrographic grating, for example a Wadsworth spectrograph. As illustrated in FIG. 10, reflecting telescope 1000 operates similarly to the first reflecting telescope of FIG. 8. Excitation light causes a sample 1020 to emit light, for example in the form of a fluorescence 1025. Reflecting telescope 1000 can be disposed such that concave reflector 1030 collects a portion of fluorescence 1025. Concave reflector 1030 reflects the collected portion of fluorescence towards convex reflector 1040. Convex reflector 1040 collects fluorescence 1035, reflected by concave reflector 1030, and reflects the collected fluorescence through the aperture in concave reflector 1030. The fluorescence 1041 that passes through the aperture can be reflected by spectrographic grating 1060 towards spectrographic detector 1062. Spectrographic grating 1060 and spectrographic detector 1062 can be aligned along the grating normal 1064. Spectrographic grating 1060 breaks up fluorescence 1041 into light of different wavelengths that can range between first wavelength light 1066 and second wavelength light 1068. This eliminates a focusing lens from the capture of the fluorescence and provides color separation and image formation in one optical element.

In various embodiments, the present teachings can provide methods for detecting fluorescence from biological samples that can be performed by the devices described above. For example, methods according to the present teachings can include providing a variety of optical components described above for reflecting, collimating, collecting, filtering, focusing, diffracting, and transmitting excitation light and/or fluorescence, as well as, exciting fluorophores and detecting fluorescence based upon the operation of the optical components described above.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An optical device for fluorescence detection from biological samples, the device comprising:
 a detector;
 an optical relay optically coupled to the detector, the optical relay comprising:
  a convex reflector;
  a first concave reflector; and a second concave reflector, wherein the second concave reflector comprises a first filter that reflects fluorescence emitted by fluorophores and that transmits an excitation light; and an excitation light source disposed such that the excitation light optically couples through the second concave reflector of the optical relay.

2. The optical device of claim 1, further comprising a first optical element to concentrate the excitation light on the second concave reflector.

3. The optical device of claim 1, further comprising a second optical element disposed to reflect the excitation light and fluorescence emitted by fluorophores.

4. The optical device of claim 1, further comprising a second optical relay optically coupled to the optical relay and the detector, the second optical relay comprising:
a second convex reflector;
a third concave reflector; and
a fourth concave reflector.

5. The optical device of claim 4, wherein the second convex reflector comprises a diffraction grating.

6. The optical device of claim 4, wherein the third and fourth concave reflectors are concave mirrors.

7. The optical device of claim 4, further comprising a second filter disposed to transmit fluorescence emitted by fluorophores and to reflect the excitation light.

8. The optical device of claim 4, wherein at least one of the first optical relay and the second optical relay comprises an Offner relay.

9. The optical device of claim 1, wherein the excitation light comprises a slit backlit by a lamp.

10. The optical device of claim 1, further comprising a light pipe to increase irradiance of collimated light to a region.

11. The optical device of claim 1, further comprising a mixing rod to increase uniformity of the excitation light.

12. An optical device for fluorescence detection from biological samples, the device comprising:
a excitation light source;
a detector; and
an optical relay optically coupled to the excitation light source and the detector, the optical relay comprising:
a concave reflector, and
a convex reflector, wherein the convex reflector comprises a diffraction grating.

13. The optical device of claim 12, wherein the concave reflector comprises a first mirror and a second mirror.

14. The optical device of claim 12, further comprising a first filter disposed to transmit an excitation light from the excitation light source and to reflect fluorescence emitted by fluorophores.

15. The optical device of claim 12, further comprising a second filter disposed to reflect an excitation light from the excitation light source and to transmit fluorescence emitted by fluorophores.

16. The optical device of claim 12, wherein the excitation light source comprises a slit, wherein the slit is backlit by a lamp.

17. The optical device of claim 12, further comprising a light pipe to increase irradiance of collimated excitation light to a region.

18. The optical device of claim 12, further comprising a mixing rod to increase uniformity of the excitation light.

19. The optical device of claim 12, further comprising a second optical relay optically coupled to the optical relay and the detector, wherein the second optical relay comprises:

a second convex reflector; and
a second concave reflector.

20. The optical device of claim 19, wherein the second concave reflector comprises a first mirror and a second mirror.

21. The optical device of claim 19, wherein at least one of the first optical relay and the second optical relays comprises an Offner relay.

22. An optical device for fluorescence detection from biological samples, the device comprising:
an excitation light source;
a detector;
an optical relay optically coupled to the excitation light source and the detector, the optical relay comprising:
a convex reflector,
a first concave reflector, and
a second concave reflector; and
a lens disposed to vary a collection angle of the optical device, wherein the lens transmits fluorescence emitted by fluorophores and reflects an excitation light from the excitation light source.

23. The optical device of claim 22, wherein the lens comprises an aplanat disposed adjacent to the first concave reflector.

24. The optical device of claim 22, further comprising a filter disposed to transmit an excitation light from the excitation light source and reflect fluorescence emitted by fluorophores.

25. An optical device for fluorescence detection from biological samples, the device comprising:
an excitation light source;
a detector;
an optical relay, comprising
a convex reflector,
a first concave reflector, and
a second concave reflector; and
a lens disposed to vary a collection angle of the optical device
a second optical relay, wherein the second optical relay comprises:
a further convex reflector; and
a further concave reflector, wherein the further convex reflector includes a diffraction grating.

26. The optical device of claim 25, wherein the further concave reflector comprises a first mirror and a second mirror.

27. The optical device of claim 22, further comprising at least one of a light pipe to increase irradiance of the collimated excitation light and a mixing rod to increase uniformity of the excitation light.

28. The optical device of claim 22, wherein at least one of the first optical relay and the second optical relay comprises an Offner relay.

29. An optical device for fluorescence detection from biological samples, the device comprising:
an excitation light source disposed to excite fluorophores to emit fluorescence;
a detector;
a first Schwarzschild telescope disposed to collect fluorescence emitted by fluorophores;
a wavelength separation system disposed to reject the excitation light and transmit fluorescence collected by the first Schwarzschild telescope; and a focusing system disposed to focus fluorescence transmitted by the wavelength separation system onto the detector.

30. The optical system of claim 29, wherein the focusing system comprises a second Schwarzschild telescope.

31. The optical system of claim 30, wherein at least one of the first Schwarzschild telescope and the second Schwarzschild telescope comprises a concave reflector comprising an aperture.

32. The optical system of claim 29, wherein the focusing system comprises at least one of a refractive, reflective, or catadioptric optical system.

33. The optical system of claim 32, wherein the wavelength separation system comprises a diffraction grating.

34. The optical system of claim 32, wherein the wavelength separation system comprises a dispersive prism.

35. The optical system of claim 32, wherein the wavelength separation system comprises at least one of a shortpass filter, a longpass filter, and a bandpass filter.

36. The optical system of claim 35, wherein the filter is disposed to provide the rejected excitation light to the first Schwarzschild telescope for focusing on the sample.

37. The optical system of claim 29, further comprising an optical element disposed to direct light from a convex mirror of the first Schwarzschild telescope to a limiting aperture of the focusing system.

38. The optical system of claim 29, wherein the first Schwarzschild telescope is unobstructed.

39. The optical system of claim 29, wherein the focusing system is a Wadsworth spectrograph.

* * * * *